(12) United States Patent
Dhonneur (10) Patent No.: US 9,326,670 B2
(45) Date of Patent: May 3, 2016

(54) GLOTTISCOPE

(71) Applicant: The Laryngeal Mask Company Limited, Victoria, Mahe (SC)

(72) Inventor: Gilles Dhonneur, Le Plessis Trevise (FR)

(73) Assignee: The Laryngeal Mask Company Limited, Victoria, Mahe (SC)

( * ) Notice: Subject to any disclaimer, the term of this patent is extended or adjusted under 35 U.S.C. 154(b) by 0 days.

(21) Appl. No.: 14/289,554

(22) Filed: May 28, 2014

(65) Prior Publication Data

US 2014/0378770 A1    Dec. 25, 2014

Related U.S. Application Data

(63) Continuation of application No. 12/996,003, filed as application No. PCT/IB2009/006102 on Jun. 4, 2009, now Pat. No. 8,777,848.

(30) Foreign Application Priority Data

Jun. 6, 2008 (GB) .................................. 0810446.5

(51) Int. Cl.
  *A61B 1/267*    (2006.01)
  *A61B 1/00*     (2006.01)
  (Continued)

(52) U.S. Cl.
  CPC ............ *A61B 1/2673* (2013.01); *A61B 1/00052* (2013.01); *A61B 1/00165* (2013.01); *A61B 1/04* (2013.01); *A61B 1/267* (2013.01); *A61M 16/0488* (2013.01); *A61M 16/0493* (2014.02); *A61M 16/0495* (2014.02); *A61M 2205/502* (2013.01); *A61M 2210/0656* (2013.01)

(58) Field of Classification Search
  CPC .. A61B 1/2673; A61B 1/00052; A61B 1/267; A61B 1/00165; A61B 1/04; A61M 16/0488; A61M 16/0493; A61M 16/0495; A61M 2205/502; A61M 2210/0656
  USPC ......... 600/185, 188, 190, 194, 197, 205, 210, 600/237, 191, 199, 240, 249
  See application file for complete search history.

(56) References Cited

U.S. PATENT DOCUMENTS

| 4,166,467 A | 9/1979 | Abramson |
| 4,995,388 A | 2/1991 | Brain |

(Continued)

FOREIGN PATENT DOCUMENTS

| AU | 647437 | 6/1991 |
| EP | 1 938 855 | 7/2008 |

(Continued)

*Primary Examiner* — Pedro Philogene
*Assistant Examiner* — David Comstock
(74) *Attorney, Agent, or Firm* — Knobbe, Martens, Olson & Bear, LLP (57) ABSTRACT

A Glottiscope for assisting with the insertion of an endotracheal tube or an Eschman like stylet into a patient is claimed. The Glottiscope comprises a blade which defines an internal passage for receiving an endotracheal tube or an Eschman like stylet, the blade having a proximal end and a distal end and means for viewing the patient's glottis, wherein the viewing means is disposed at the distal end and in use, below the point of emergence of an endotracheal tube or a stylet/guide (to rail road the endotracheal tube) in the internal passage to provide a view of the patient's glottis, the blade being adapted to direct the viewing means towards the center of the patient's glottis.

13 Claims, 6 Drawing Sheets

(51) Int. Cl.
*A61M 16/04* (2006.01)
*A61B 1/04* (2006.01)

(56) References Cited

U.S. PATENT DOCUMENTS

| | | | |
|---|---|---|---|
| 5,241,956 | A | 9/1993 | Brain |
| 5,318,017 | A | 6/1994 | Ellison |
| 5,355,879 | A | 10/1994 | Brain |
| 6,705,318 | B1 | 3/2004 | Brain |
| 6,955,645 | B1 * | 10/2005 | Zeitels ............ 600/187 |
| 2004/0020491 | A1 | 2/2004 | Fortuna |
| 2005/0066975 | A1 | 3/2005 | Brain |
| 2005/0081861 | A1 | 4/2005 | Nasir |
| 2005/0090712 | A1 | 4/2005 | Cubb |
| 2006/0124132 | A1 | 6/2006 | Brain |
| 2008/0041392 | A1 | 2/2008 | Cook |
| 2008/0276936 | A1 | 11/2008 | Cook |
| 2009/0090356 | A1 | 4/2009 | Cook |
| 2011/0023890 | A1 | 2/2011 | Baska |

FOREIGN PATENT DOCUMENTS

| | | |
|---|---|---|
| EP | 2 044 969 | 4/2009 |
| GB | 2 298 580 | 9/1996 |
| GB | 2 404 863 | 2/2005 |
| GB | 2 444 779 | 6/2008 |
| GB | 2 465 453 | 5/2010 |
| WO | WO 94/02191 | 2/1994 |
| WO | WO 99/27840 | 6/1999 |
| WO | WO 2004/016308 | 2/2004 |
| WO | WO 2004/089453 | 10/2004 |
| WO | WO 2005/011784 | 2/2005 |
| WO | WO 2005/046751 | 5/2005 |
| WO | WO 2008/001724 | 1/2008 |
| WO | WO 2009/026628 | 3/2009 |
| WO | WO 2010/060227 | 6/2010 |
| WO | WO 2010/066001 | 6/2010 |

\* cited by examiner

GLOTTISCOPE

This application is a continuation of U.S. patent application Ser. No. 12/996,003, filed Mar. 9, 2011, now U.S. Pat. No. 8,777,848, which is the U.S. National Phase under 35 U.S.C. §371 of International Application No. PCT/IB2009/006102, filed Jun. 4, 2009, which claims priority to the Great Britain Patent Application No. 0810446.5, filed Jun. 6, 2008.

The invention relates to a glottiscope which is an enhanced laryngoscope.

A glottiscope is a device which is used by clinicians during tracheal intubation. In the past 50 years tracheal intubation was performed using a laryngoscope. A laryngoscope allows the clinicians viewing the larynx. A glottiscope is an enhanced laryngoscope allowing the clinicians viewing the glottis which represents an organ of the larynx placed at the entrance of the trachea. During tracheal intubation, an endotracheal tube is inserted in the oral cavity, past the pharynx and larynx, through the glottis, and into the patient's trachea in order to establish an airway in a patient.

Intubation is a potentially dangerous invasive procedure that requires a lot of clinical experience to master. In many instances, difficulties in inserting an endotracheal tube have led to the death of a patient because it was not possible to establish an airway with sufficient rapidity. This is a particular problem where the patient has a so-called "difficult" airway. The main risk is that the endotracheal tube is unwittingly passed by the clinician into the patient's esophagus, rather than into the trachea. This is a particular problem in patients with an abnormally high positioned larynx and no view of the glottis.

A glottiscope assists with intubation by allowing the clinician to continuously visualise the path of the endotracheal tube as it passes through the glottis towards the trachea.

Glottiscopes which not only provide visualisation, but which also assist with intubation are known. Examples of such laryngoscopes are those sold under the trade marks Airtraq®, GlideScope® and AirwayScope®. These glottiscopes each comprise a curved blade, which is dimensioned to conform to the anatomical curve of a patient's throat when positioned with its proximal end protruding from the patient's mouth and its distal end adjacent to the glottis. The blade may include a channel which receives an endotracheal tube. The blade is made from a relatively rigid material, so that movement of the proximal end of the blade is transmitted to the distal end directly and without delay. The clinician can therefore use the blade to help manoeuvre the endotracheal tube towards the trachea. The blade also includes visualisation means to allow a clinician to view the endotracheal tube as it emerges from the distal end of the blade, and so guide it towards the glottis. The visualisation means consist of a CCD or CMOS camera in the case of the GlideScope® laryngoscope and optical elements in the case of the Airtraq® laryngoscope.

A problem with known laryngoscopes is that the visualisation means is often obscured by the emergent endotracheal tube at the crucial moment when it must be guided most precisely to ensure that it does not enter the oesophagus. It is an object of the present invention to seek to mitigate problems such as this.

Accordingly, the invention provides a glottiscope for assisting with the insertion of an endotracheal tube or an Eschman like stylet into the trachea of a patient, the glottiscope comprising a blade which defines an internal passage for receiving an endotracheal tube or a Eschman like stylet, the blade having a proximal end and a distal end and means for viewing the patient's glottis, wherein the viewing means is disposed at the distal end and in use, below the point of emergence of an endotracheal tube in the internal passage, the blade being adapted to direct the viewing means in the direction of the centre of the patient's glottis.

An Eschman like stylet is a device that may be used to guide the endotracheal tube into the trachea of a patient.

It has been found that having the viewing means disposed in use below the point of emergence of the endotracheal tube results in fewer instances of obstruction. Furthermore, as the viewing means is directed towards the centre of the patient's glottis, a better view of the glottis is obtained than is the case with the known laryngoscopes.

The blade may comprise a curved portion, which conforms to a circular arc having a radius of curvature of between 100° and 145°, preferably between 115°-425°. The internal passage of the blade may be from 0.3 to 1.5 cm in diameter.

The blade may comprise a straight portion, which is tangentially connected to the distal end of the curved portion.

The blade may comprise guide means to assist in directing an endotracheal tube towards the centre of the patient's glottis.

The guide means may comprise a ramp provided on the interior surface of the blade's passage.

The ramp may be such that, in use, it directs the distal end of an endotracheal tube towards the centre of the patient's glottis.

The ramp may be such that, in use, it raises the distal end of the endotracheal tube above the central axis of the curved portion of the blade.

The ramp may be such that, in use, it maintains the distal end of the endotracheal tube in the same plane as the central axis of the curved portion of the blade.

The angle of the ramp may be from 0 degrees to 20 degrees relative to the tube, and preferably from 10 degrees to 20 degrees relative to the tube.

The viewing means may comprise a fibre optic viewing device having a proximal end and a distal end, the distal end being located at the distal end of the blade.

The distal end of the fibre optic viewing device may be in the same plane as the central axis of the blade's passage.

The glottiscope may comprise a ramp and the distal end of the fibre optic viewing device may be positioned beneath the ramp.

The proximal end of the fibre optic viewing device may not be in the same vertical plane as the central axis of the blade's passage.

The blade may include a channel in its side which opens into the passage to assist with the removal and the insertion of an endotracheal tube into the passage. The diameter of the channel may vary between 0.2 and 1.2 cm.

The blade may include a tongue at its distal end to lift the patient's epiglottis out of the path of an endotracheal tube as it advances towards the glottis. The distance between distalend of the fibre optic viewing device and the extremity of the distal tongue may vary from 1.0 to 2.5 cm depending of the size of the glottiscope.

The invention will now be illustrated by way of example with reference to the following drawings of which.

In this application, the terms "distal part" and "proximal part" are used relative to the medical professional, e.g. the "distal part" is used to describe the part of the device that is inserted first into the patient.

The glottiscope shown in FIGS. 1 to 4 comprises a blade 1 having a proximal end and a distal end.

Figure 1:
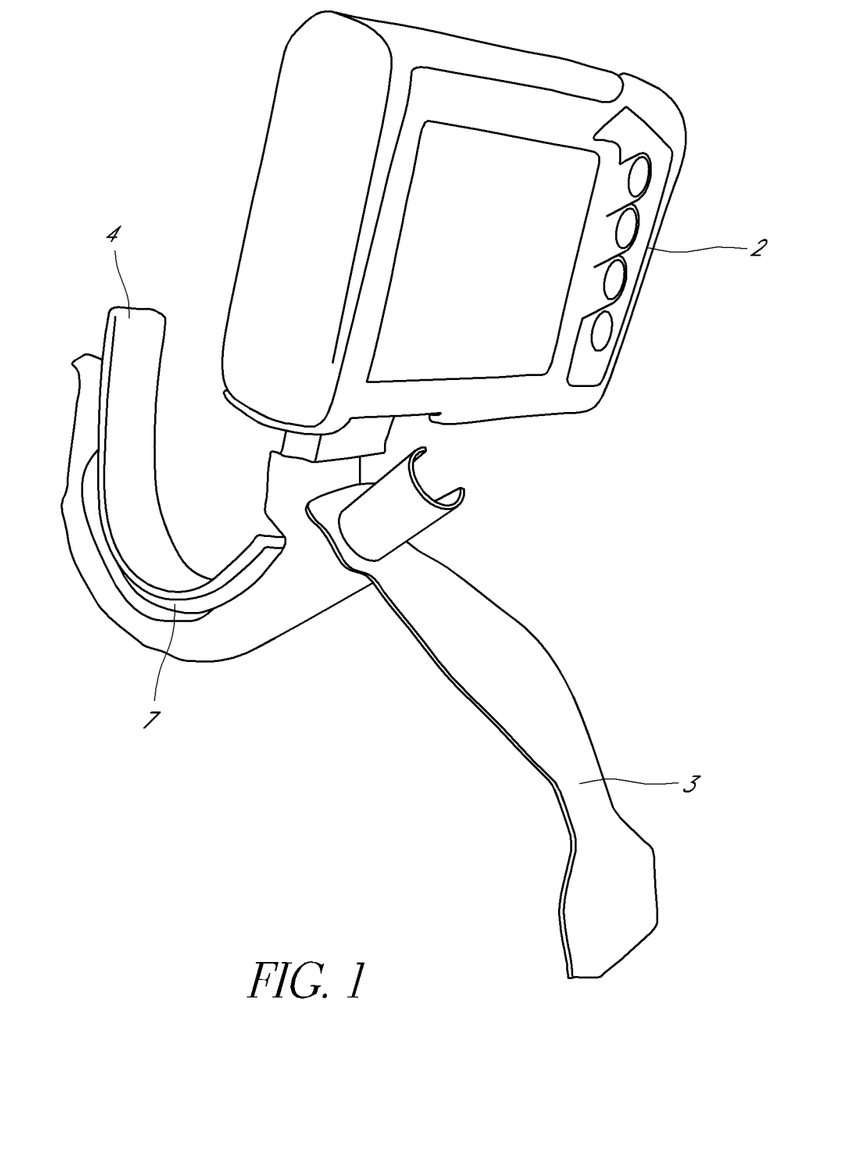
FIG. 1 shows a perspective view of a glottiscope according to the invention.

A screen 2 and a handle 3 are provided at the blade's proximal end. Preferably, the screen 2 is pivotable and the handle 3 is fixed. This embodiment has a viewing means comprising a fibre optic viewing device but within the context of the invention, the viewing means may include any of a fibre optic device, camera, such as CCD digital camera, viewing screen, CMOS device and/or other viewing means. A WIFI connection between the glottiscope optics and the viewing screen may be used.

Figure 4:
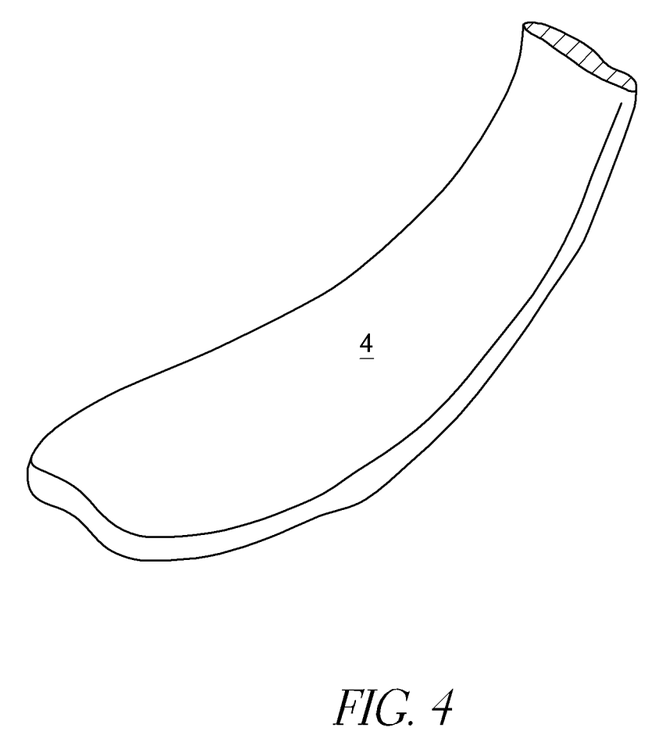
FIG. 4 shows a preferred tongue for use with the glottiscope.

A tongue 4 is provided at the blade's distal end to lift the patient's epiglottis out of the path of the endotracheal tube as it advances towards the glottis. As shown in FIG. 4, the tongue 4 where it is used to engage the epiglottis may be shaped to fit around the ligament for example by having an indented distal end. This makes location easier and reduces trauma to the ligament. Preferably the shaped of the tongue is rounded, i.e. it does not have any sharp edges that might injure the patient. A disposable cuff 5 is placed over the distal end of the blade 1 to minimise the necessary cleaning of the device and airway mucous protection. This disposable cuff inflation line runs inside the channel driving the endotracheal tube.

The blade 1 is hollow, having a passage 6 there through for receiving an endotracheal tube or any flexible semi-rigid or angulated Eschman like stylet allowing access to the glottis and trachea to railroad the endotracheal tube. The blade 1 includes an opening 7 along one side which opens into the passage 6 to facilitate removal and insertion of an endotracheal tube into the passage 6.

The blade 1 is made from a plastics material which is sufficiently rigid that movement of the proximal end of the blade 1 is transmitted to the distal end of the blade 1 directly and without delay.

The blade 1 comprises a first straight portion 8 at its proximal end, a second straight portion 9 at its distal end, and a curved central portion 10 in between the two straight portions.

The curved central portion 10 of the blade 1 is dimensioned to conform to the anatomical curve of a patient's throat between the hard palate at the proximal end of the blade 1 and the laryngeal inlet at the distal end of the blade 1. Thus, the central portion 10 conforms to a circular arc having a radius of curvature of about 120°, the curvature being along the central axis 11 of the blade's passage 6 and in a vertical plane of symmetry. The two straight portions 8, 9 of the blade 1 are tangentially connected to the central curved portion 10. In the most preferred embodiment of the invention, the radius of curvature is about 32.35 mm and sweeps through an angle of preferably from 115° to 125°, most preferably of 120°.

Figure 2:
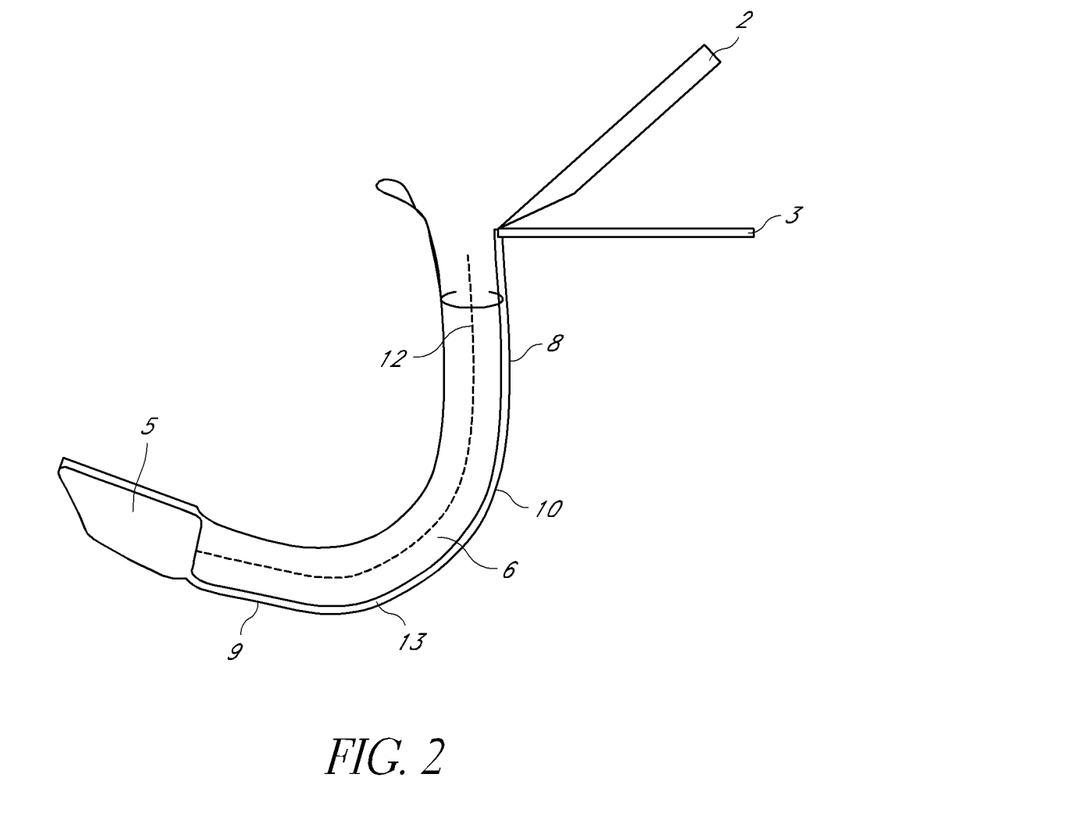
FIG. 2 shows a schematic side view of part of the glottiscope of FIG. 1.
Figure 3:
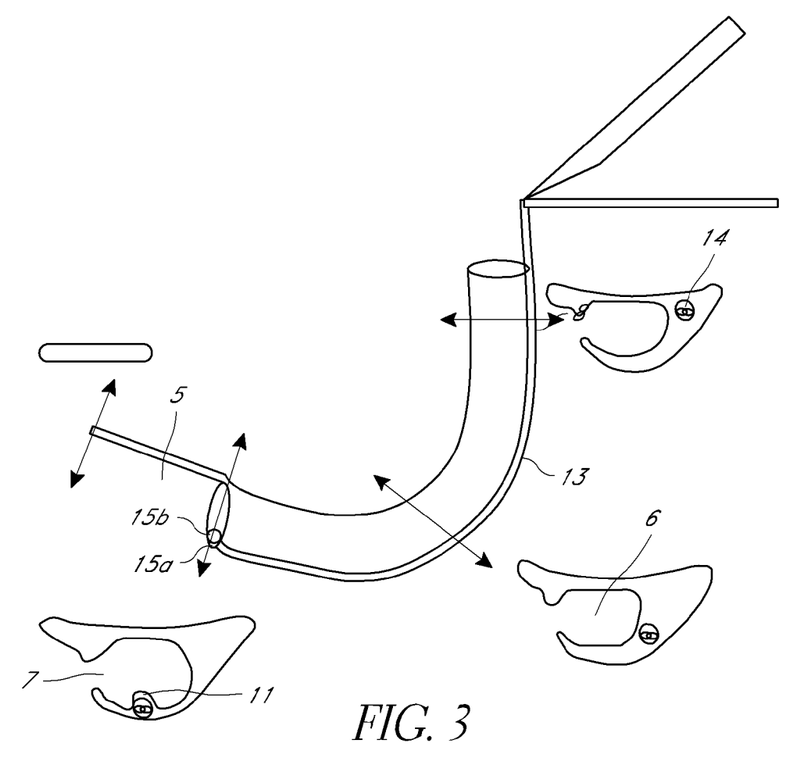
FIG. 3 shows a schematic side view and a number of cross-sectional views of part of the glottiscope of FIG. 1.

As shown in FIGS. 2 and 3, a ramp 11 is provided on the interior surface of the blade's passage 6 to guide an endotracheal tube which has been inserted in the blade 1 towards the centre of the glottis. The ramp 11 is such that it raises the distal end of the endotracheal tube or the Eschman like stylet above the central axis 12 of the curved portion 10 of the blade 1, while maintaining it in the same plane as said central axis 12. The angle of the ramp 11 adds about 17° to the curvature of the curved portion 10.

Similarly, a ramp 11 may be provided on the interior surface of the blade's passage 6 but such that it deflects the distal end of the endotracheal tube or the Eschman like stylet below the central axis 12 of the curved portion 10 of the blade 1, while maintaining it in the same plane as said central axis 12.

A fibre optic viewing device 13 is mounted in a narrow passage 14 which is provided in the walls of the blade 1. As can be seen from FIG. 3, the viewing device is disposed below (in use) the point of emergence of an endotracheal tube or an Eschman like stylet.

The fibre optic viewing device 13 comprises two bundles of optical fibres 15a, 15b which extend from the proximal end of the blade 1 to the distal end. The proximal end of the fibres 15 a,b is attached to the screen 2. The distal end of the fibres 15 a,b is attached to a lens (not shown). One of the bundles of fibres 15a carries light from the proximal end to the lens so as to illuminate the patient's throat. The other of the bundles of fibres 15b carries light received by the lens back to the proximal end so as to provide a view of the patient's throat.

Figure 5:
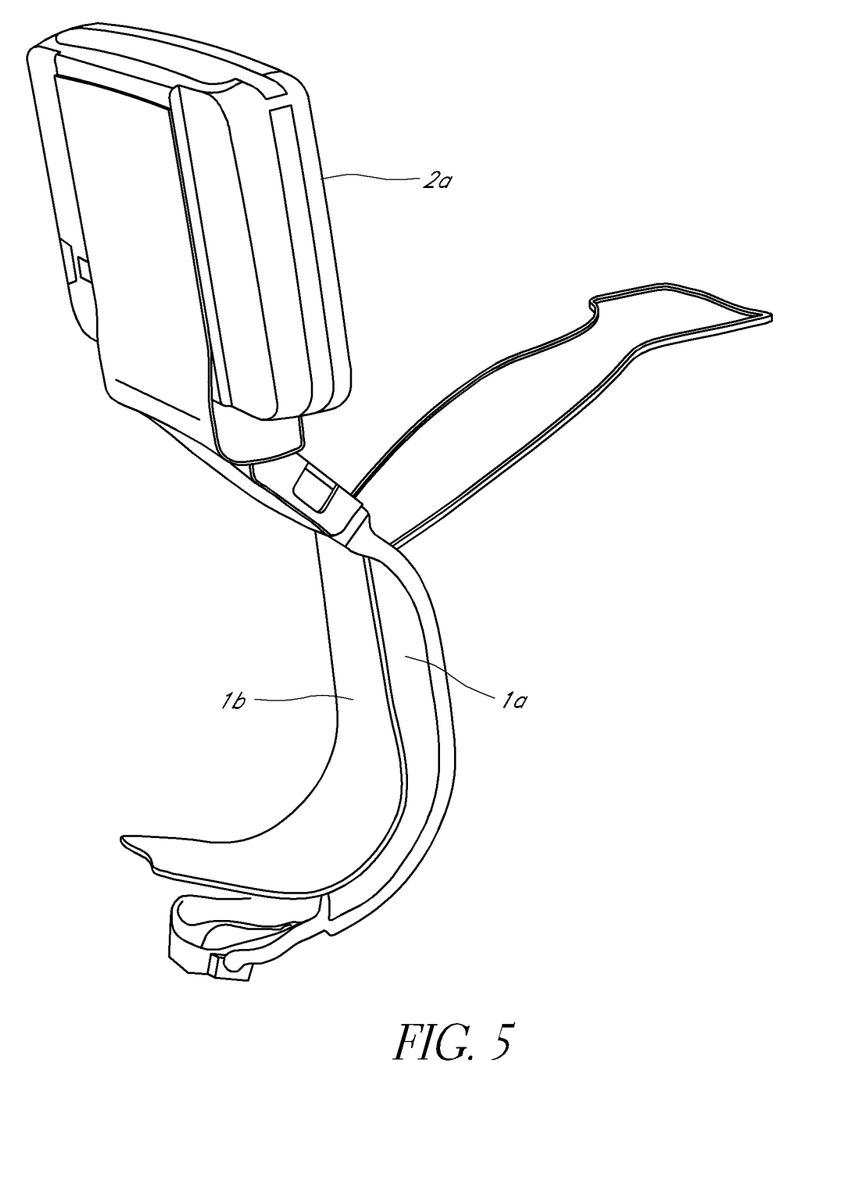
FIG. 5 is a perspective view of a second glottiscope according to the invention.
Figure 6:
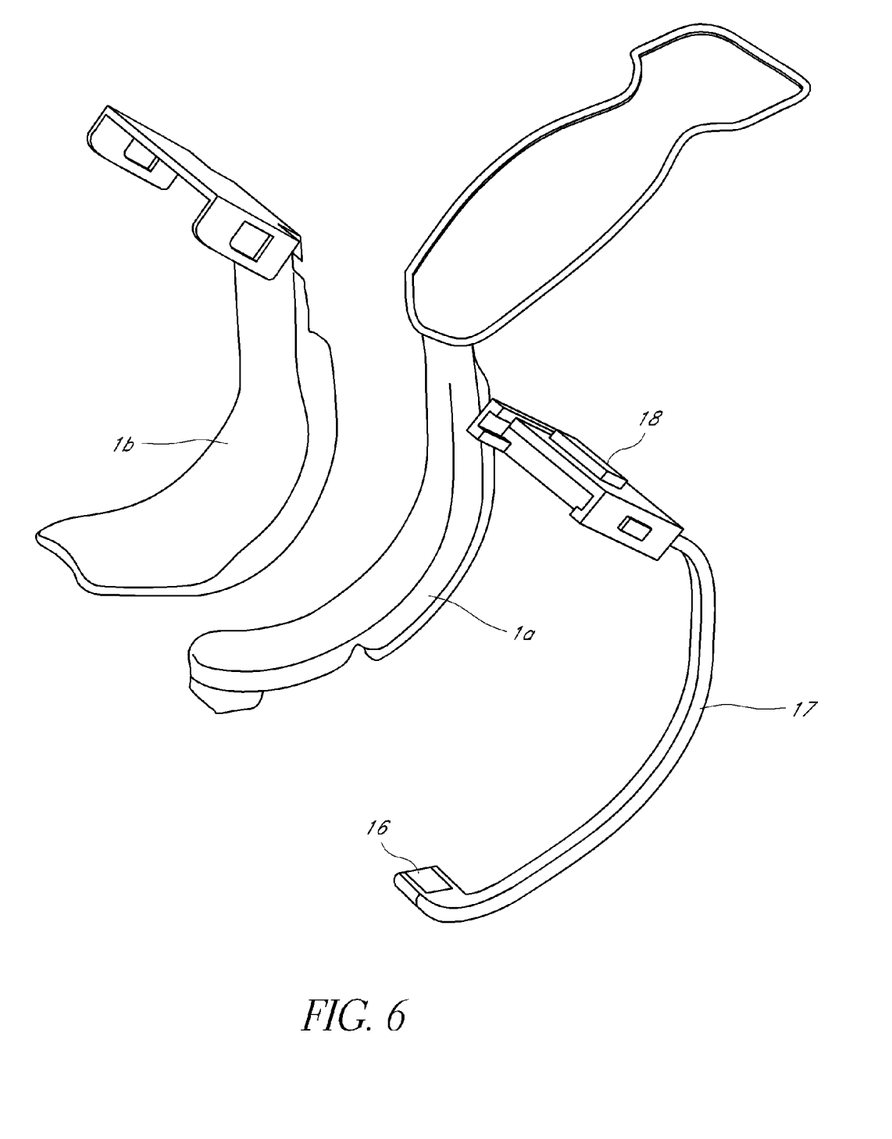
FIG. 6 is an exploded view of the glottiscope of FIG. 5.

The device shown in FIGS. 5 and 6 comprises the following elements: a two-part blade 1 a,b, a handle 3a and the viewing means. In this specific embodiment, the viewing means comprises a CMOS device 16 placed at the distal end of a flexible tube 17, preferably made of steel, plastic or silicon, and a display screen 2a removably connected to the tube 17 via a suitable connection means 18. The flexible tube 17 is enclosed between the two parts forming the blade 1 a,b so that the display screen can be connected at the proximal end of the blade and the CMOS device at the distal end of the blade so as to provide a view of the patient's throat.

At the proximal end of the blade 1, the passage 6 is offset from the plane of the central axis 12 of the blade's passage 6. However, as it progresses along the blade 1, it assumes a more central location, so that, by the distal end of the blade 1, it is in the same vertical plane as the central axis 12 of the blade's passage 6. This ensures that the patient's teeth do not contact and damage the optical fibres 15 a,b at the proximal end of the blade 1, while at the same time ensuring that the lens, which is positioned at the distal end of the blade 1, is positioned directly beneath the ramp 11.

In operation, an endotracheal tube or an Eschman like stylet is inserted into the blade's passage 6. The distal end of the blade 1 is then inserted through the patient's mouth into the patient's pharynx, while the proximal end of the blade 1 remains outside of the patient's mouth. If necessary, the handle 3 may be used to help manoeuvre the distal end of the blade 1 into the correct position.

Once the blade 1 is in the correct position, the endotracheal tube is advanced along the blade's passage 6 until it emerges from the blade's passage 6 and towards the patient's glottis.

The fibre optic viewing device 13 illuminates the patient's throat and provides the clinician with a view of the patient's glottis on the screen 2 to allow the clinician to visualise the path of the endotracheal tube or the Eschman like stylet as it approaches the glottis.

As the ramp 11 is directed towards the centre of the glottis, and the lens is positioned beneath the ramp, this means that the lens will also be directed towards the centre of the glottis. This will assist in viewing the glottis.

Moreover, because of the shape of the blade 1, a wider area of the patient's throat will be illuminated and viewed. Thus, the area posterior to the pharynx and anterior to the larynx will be illuminated and viewed.

The glottiscope shown in FIGS. 1 to 3 is designed to be disposable. However, it is also possible to have a reusable device, which may be sterilised and reused many times.

The above embodiment is described by way of example. A number of possible variations will be apparent to the skilled person without departing from the scope of the claims.

The invention claimed is:

1. A glottiscope for assisting with the insertion of an endotracheal tube or an Eschman stylet into a patient, the glottiscope comprising a blade which defines an internal passage for receiving the tube or the stylet, the blade having a proximal end and a distal end and means for viewing the patient's glottis, wherein the viewing means is disposed at the distal end and in use, below the point of emergence of the tube or the stylet in the internal passage to provide a view of the patient's glottis, the blade being adapted to direct the viewing means towards the centre of the patient's glottis, wherein the blade includes an opening along one side which opens into the passage to assist with removal and insertion of an endotracheal tube or an Eschman stylet into the passage.

2. The glottiscope according to claim 1, wherein the blade comprises a curved portion conforming to a circular arc having a radius of curvature of between 100° and 145°.

3. The glottiscope according to claim 1, wherein the blade comprises a ramp provided on the interior surface of the blade's passage.

4. The glottiscope according to claim 3, wherein the ramp is such that, in use, it directs the distal end of an endotracheal tube or an Eschman stylet/guide towards the centre of the patient's glottis.

5. The glottiscope according to claim 4, wherein the ramp is such that, in use, it raises the distal end of the endotracheal tube or an Eschman stylet above the central axis of a curved portion of the blade.

6. The glottiscope according to claim 4, wherein the ramp is such that, in use, it maintains the distal end of the endotracheal tube or an Eschman stylet in the same plane as the central axis of a curved portion of the blade.

7. The glottiscope according to claim 3, wherein the angle of the ramp is from 0 degrees to 20 degrees.

8. The glottiscope according to claim 1, wherein the viewing means comprise a fibre optic viewing device having a proximal end and a distal end, the distal end being located at the distal end of the blade.

9. The glottiscope according to claim 8, wherein the distal end of the fibre optic viewing device is in the same plane as the central axis of the blade's passage.

10. The glottiscope according to claim 8, wherein the glottiscope comprises a ramp and the distal end of the fibre optic viewing device is positioned beneath the ramp.

11. The glottiscope according to claim 8, wherein the proximal end of the fibre optic viewing device is not in the same vertical plane as the central axis of the blade's passage.

12. The glottiscope according to claim 1, wherein the blade includes a tongue at its distal end to lift the patient's epiglottis out of the path of an endotracheal tube or an Eschman stylet/guide as it advances towards the glottis.

13. The glottiscope according to claim 1, wherein the blade comprises a curved portion conforming to a circular arc having a radius of curvature of between 115°-125.

* * * * *